(12) United States Patent
Pratt (10) Patent No.: US 11,131,729 B2
(45) Date of Patent: Sep. 28, 2021

(54) SYSTEMS AND METHODS WITH ANGLED INPUT BEAMS FOR AN OPTICALLY PUMPED MAGNETOMETER

(71) Applicant: HI LLC, Los Angeles, CA (US)

(72) Inventor: Ethan Pratt, Santa Clara, CA (US)

(73) Assignee: HI LLC, Los Angeles, CA (US)

( * ) Notice: Subject to any disclaimer, the term of this patent is extended or adjusted under 35 U.S.C. 154(b) by 0 days.

(21) Appl. No.: 16/904,281

(22) Filed: Jun. 17, 2020

(65) Prior Publication Data

US 2020/0400763 A1 Dec. 24, 2020

Related U.S. Application Data

(60) Provisional application No. 62/913,000, filed on Oct. 9, 2019, provisional application No. 62/865,049, filed on Jun. 21, 2019.

(51) Int. Cl.
*G01R 33/26* (2006.01)

(52) U.S. Cl.
CPC .................. *G01R 33/26* (2013.01)

(58) Field of Classification Search
CPC .. G01R 33/26; G01R 33/0094; G01R 33/032; A61B 2562/0223; A61B 5/245; G02B 27/14; G02B 5/04; G01N 24/006
See application file for complete search history.

(56) References Cited

U.S. PATENT DOCUMENTS

| | | |
|---|---|---|
| 3,173,082 A | 3/1965 | Bell et al. |
| 3,257,608 A | 6/1966 | Bell et al. |
| 3,495,161 A | 2/1970 | Bell |
| 3,501,689 A | 3/1970 | Robbiano |
| 3,513,381 A | 5/1970 | Happer, Jr. |
| 4,193,029 A | 3/1980 | Cioccio et al. |
| 4,951,674 A | 8/1990 | Zanakis et al. |
| 5,189,368 A | 2/1993 | Chase |

(Continued)

FOREIGN PATENT DOCUMENTS

| | | |
|---|---|---|
| CN | 104730484 | 6/2015 |
| CN | 107562188 | 1/2018 |

(Continued)

OTHER PUBLICATIONS

Okada, Y.C., Lahteenmäki, A. and Xu, C., "Experimental analysis of distortion of magnetoencephalography signals by the skull." Clinical neurophysiology 110 (2), 230-238 (1999).

(Continued)

*Primary Examiner* — Jay Patidar
(74) *Attorney, Agent, or Firm* — Branch Partners PLLC; Bruce E. Black (57) ABSTRACT

An optically pumped magnetometer device includes a first vapor cell having a light input window; a first light source configured to produce a first light beam; a first prism optic configured to receive the first light beam from the first light source and redirect the first light beam into the first vapor cell at a non-normal direction relative to the light input window of the first vapor cell; and a first light detector configured to receive the first light beam after passing through the first vapor cell. The device may also include additional light sources and light detectors which may share the prism optic and vapor cell (or utilize another prism optic or vapor cell or both).

20 Claims, 5 Drawing Sheets

(56) References Cited

U.S. PATENT DOCUMENTS

| | | |
|---|---|---|
| 5,192,921 A | 3/1993 | Chantry et al. |
| 5,225,778 A | 7/1993 | Chaillout et al. |
| 5,254,947 A | 10/1993 | Chaillout et al. |
| 5,309,095 A | 5/1994 | Ahonen et al. |
| 5,442,289 A | 8/1995 | Dilorio et al. |
| 5,444,372 A | 8/1995 | Wikswo, Jr. et al. |
| 5,471,985 A | 12/1995 | Warden |
| 5,506,200 A | 4/1996 | Hirschkoff et al. |
| 5,526,811 A | 6/1996 | Lypchuk |
| 5,713,354 A | 2/1998 | Warden |
| 6,144,872 A | 11/2000 | Graetz |
| 6,339,328 B1 | 1/2002 | Keene et al. |
| 6,472,869 B1 | 10/2002 | Upschulte et al. |
| 6,665,553 B2 | 12/2003 | Kandori et al. |
| 6,806,784 B2 | 10/2004 | Hollberg et al. |
| 6,831,522 B2 | 12/2004 | Kitching et al. |
| 7,038,450 B2 | 5/2006 | Romalis et al. |
| 7,102,451 B2 | 9/2006 | Happer et al. |
| 7,145,333 B2 | 12/2006 | Romalis et al. |
| 7,521,928 B2 | 4/2009 | Romalis et al. |
| 7,656,154 B2 | 2/2010 | Kawabata et al. |
| 7,826,065 B1 | 11/2010 | Okandan et al. |
| 7,872,473 B2 | 1/2011 | Kitching et al. |
| 7,994,783 B2 | 8/2011 | Ledbetter et al. |
| 8,054,074 B2 | 11/2011 | Ichihara et al. |
| 8,212,556 B1 | 7/2012 | Schwindt et al. |
| 8,258,884 B2 | 9/2012 | Borwick, III et al. |
| 8,319,156 B2 | 11/2012 | Borwick, III et al. |
| 8,334,690 B2 | 12/2012 | Kitching et al. |
| 8,373,413 B2 | 2/2013 | Sugioka |
| 8,405,389 B2 | 3/2013 | Sugioka et al. |
| 8,587,304 B2 | 11/2013 | Budker et al. |
| 8,836,327 B2 | 9/2014 | French et al. |
| 8,906,470 B2 | 12/2014 | Overstolz et al. |
| 8,941,377 B2 | 1/2015 | Mizutani et al. |
| 9,084,549 B2 | 7/2015 | Desain et al. |
| 9,095,266 B1 | 8/2015 | Fu |
| 9,116,201 B2 | 8/2015 | Shah et al. |
| 9,140,590 B2 | 9/2015 | Waters et al. |
| 9,140,657 B2 | 9/2015 | Ledbetter et al. |
| 9,169,974 B2 | 10/2015 | Parsa et al. |
| 9,244,137 B2 | 1/2016 | Kobayashi et al. |
| 9,291,508 B1 | 3/2016 | Biedermann et al. |
| 9,343,447 B2 | 3/2016 | Parsa et al. |
| 9,366,735 B2 | 6/2016 | Kawabata et al. |
| 9,383,419 B2 | 7/2016 | Mizutani et al. |
| 9,395,425 B2 | 7/2016 | Diamond et al. |
| 9,417,293 B2 | 8/2016 | Schaffer et al. |
| 9,429,918 B2 | 8/2016 | Parsa et al. |
| 9,568,565 B2 | 2/2017 | Parsa et al. |
| 9,575,144 B2 | 2/2017 | Kornack et al. |
| 9,601,225 B2 | 3/2017 | Parsa et al. |
| 9,638,768 B2 | 5/2017 | Foley et al. |
| 9,639,062 B2 | 5/2017 | Dyer et al. |
| 9,677,905 B2 | 6/2017 | Waters et al. |
| 9,726,626 B2 | 8/2017 | Smith et al. |
| 9,726,733 B2 | 8/2017 | Smith et al. |
| 9,791,536 B1 | 10/2017 | Alem et al. |
| 9,829,544 B2 | 11/2017 | Bulatowicz |
| 9,846,054 B2 | 12/2017 | Waters et al. |
| 9,851,418 B2 | 12/2017 | Wolf et al. |
| 9,869,731 B1 | 1/2018 | Hovde et al. |
| 9,915,711 B2 | 3/2018 | Kornack et al. |
| 9,927,501 B2 | 3/2018 | Kim et al. |
| 9,948,314 B2 | 4/2018 | Dyer et al. |
| 9,964,609 B2 | 5/2018 | Ichihara et al. |
| 9,964,610 B2 | 5/2018 | Shah et al. |
| 9,970,999 B2 | 5/2018 | Larsen et al. |
| 9,995,800 B1 | 6/2018 | Schwindt et al. |
| 10,024,929 B2 | 7/2018 | Parsa et al. |
| 10,088,535 B1 | 10/2018 | Shah |
| 10,162,016 B2 | 12/2018 | Gabrys et al. |
| 10,194,865 B2 | 2/2019 | Le et al. |
| 10,314,508 B2 | 6/2019 | Desain et al. |
| 10,371,764 B2 | 8/2019 | Morales et al. |
| 10,772,561 B2 | 9/2020 | Donaldson |
| 2004/0232912 A1 | 11/2004 | Tsukamoto et al. |
| 2005/0007118 A1 | 1/2005 | Kitching et al. |
| 2005/0046851 A1 | 3/2005 | Riley, Jr. et al. |
| 2005/0206377 A1 | 9/2005 | Romalis et al. |
| 2007/0076776 A1 | 4/2007 | Lust et al. |
| 2007/0120563 A1 | 5/2007 | Kawabata et al. |
| 2007/0167723 A1 | 7/2007 | Park et al. |
| 2007/0205767 A1 | 9/2007 | Xu et al. |
| 2009/0079426 A1 | 3/2009 | Anderson |
| 2009/0101806 A1 | 4/2009 | Masuda |
| 2010/0219820 A1 | 9/2010 | Skidmore et al. |
| 2011/0062956 A1 | 3/2011 | Edelstein et al. |
| 2012/0112749 A1 | 5/2012 | Budker et al. |
| 2013/0082700 A1 | 4/2013 | Mizutani et al. |
| 2013/0082701 A1 | 4/2013 | Mizutani et al. |
| 2013/0207649 A1* | 8/2013 | Mizutani ............ G01R 33/032 324/244.1 |
| 2013/0265042 A1 | 10/2013 | Kawabata et al. |
| 2014/0121491 A1 | 5/2014 | Zhang |
| 2014/0306700 A1 | 10/2014 | Kamada et al. |
| 2014/0354275 A1 | 12/2014 | Sheng et al. |
| 2015/0022200 A1 | 1/2015 | Ichihara et al. |
| 2015/0054504 A1 | 2/2015 | Ichihara et al. |
| 2015/0378316 A1 | 12/2015 | Parsa et al. |
| 2016/0061913 A1 | 3/2016 | Kobayashi et al. |
| 2016/0116553 A1 | 4/2016 | Kim et al. |
| 2016/0223627 A1 | 8/2016 | Shah et al. |
| 2016/0291099 A1* | 10/2016 | Ueno .................. A61B 5/055 |
| 2016/0313417 A1 | 10/2016 | Kawabata et al. |
| 2017/0023653 A1 | 1/2017 | Kobayashi et al. |
| 2017/0023654 A1 | 1/2017 | Kobayashi et al. |
| 2017/0067969 A1 | 3/2017 | Butters et al. |
| 2017/0199138 A1 | 7/2017 | Parsa et al. |
| 2017/0199251 A1 | 7/2017 | Fujii et al. |
| 2017/0261564 A1 | 9/2017 | Gabrys et al. |
| 2017/0331485 A1 | 11/2017 | Gobet et al. |
| 2017/0343617 A1 | 11/2017 | Manickam et al. |
| 2017/0343695 A1 | 11/2017 | Stetson et al. |
| 2017/0356969 A1 | 12/2017 | Ueno |
| 2017/0360322 A1 | 12/2017 | Ueno |
| 2017/0363695 A1 | 12/2017 | Ueno |
| 2018/0003777 A1 | 1/2018 | Sorenson et al. |
| 2018/0038921 A1 | 2/2018 | Parsa et al. |
| 2018/0100749 A1 | 4/2018 | Waters et al. |
| 2018/0128885 A1 | 5/2018 | Parsa et al. |
| 2018/0156875 A1 | 6/2018 | Herbsommer et al. |
| 2018/0219353 A1 | 8/2018 | Shah |
| 2018/0238974 A1 | 8/2018 | Shah et al. |
| 2018/0313908 A1 | 11/2018 | Knappe et al. |
| 2018/0313913 A1 | 11/2018 | DeNatale et al. |
| 2018/0372813 A1 | 12/2018 | Bulatowicz et al. |
| 2019/0391213 A1 | 12/2019 | Alford |
| 2020/0025844 A1 | 1/2020 | Alford et al. |
| 2020/0057115 A1 | 2/2020 | Jiménez-Martínez et al. |
| 2020/0057116 A1 | 2/2020 | Zorzos et al. |
| 2020/0064421 A1 | 2/2020 | Kobayashi et al. |
| 2020/0072916 A1 | 3/2020 | Alford et al. |
| 2020/0088811 A1 | 3/2020 | Mohseni |
| 2020/0241094 A1 | 7/2020 | Alford |
| 2020/0256929 A1 | 8/2020 | Ledbetter et al. |
| 2020/0309873 A1 | 10/2020 | Ledbetter et al. |
| 2020/0334559 A1 | 10/2020 | Anderson et al. |
| 2020/0341081 A1 | 10/2020 | Mohseni et al. |
| 2020/0381128 A1 | 12/2020 | Pratt et al. |
| 2020/0400763 A1 | 12/2020 | Pratt |
| 2021/0063510 A1 | 3/2021 | Ledbetter |

FOREIGN PATENT DOCUMENTS

| | | |
|---|---|---|
| EP | 2738627 A3 | 6/2014 |
| EP | 2380029 B1 | 10/2015 |
| EP | 3037836 B1 | 9/2017 |
| JP | 2016109665 | 6/2016 |
| JP | 2018004462 | 1/2018 |
| WO | 2005/081794 | 9/2005 |

(56) References Cited

FOREIGN PATENT DOCUMENTS

| WO | 2014/031985 | 2/2014 |
|---|---|---|
| WO | 2017/095998 | 6/2017 |

OTHER PUBLICATIONS

Robinson, J.T., Pohlmeyer, E., Gather, M.C., Kemere, C., Kitching, J.E., Malliaras, G.G., Marblestone, A., Shepard, K. L., Stieglitz, T. and Xie, C., "Developing Next-Generation Brain Sensing Technologies—A Review." IEEE sensors journal, 19(22), 10163-10175 (2019).

Shah, V., Knappe, S., Schwindt, P.D. and Kitching, J., "Subpicotesla atomic magnetometry with a microfabricated vapour cell." Nature Photon 1, 649-652 (2007).

Griffith, W.C., Knappe, S. and Kitching, J., "Femtotesla atomic magnetometry in a microfabricated vapor cell." Optics express 18, (26), 27167-27172 (2010).

Tierney, T.M., Holmes, N., Mellor, S., López, J.D., Roberts, G., Hill, R.M., Boto, E., Leggett, J., Shah, V., Brookes, M.J. and Bowtell, R., "Optically pumped magnetometers: From quantum origins to multichannel magnetoencephalography." NeuroImage, 199, 598-608 (2019).

Iivanainen, J., Zetter, R., Grön, M., Hakkarainen, K. and Parkkonen, L., "On-scalp MEG system utilizing an actively shielded array of optically-pumped magnetometers." Neuroimage 194, 244-258 (2019).

Iivanainen, J., Stenroos, M. and Parkkonen, L., "Measuring MEG closer to the brain: Performance of on-scalp sensor arrays." NeuroImage 147, 542-553 (2017).

Kitching, J., Knappe, S., Gerginov, V., Shah, V., Schwindt, P.D., Lindseth, B., Donley E.A., "Chip-scale atomic devices: precision atomic instruments based on MEMS." In Frequency Standards and Metrology, 445-453 (2009).

Kitching, J., Knappe, S. and Donley, E.A., "Atomic sensors—a review." IEEE Sensors Journal, 11(9), 1749-1758 (2011).

Budker, D. and Romalis, M., "Optical magnetometry". Nature physics, 3(4), 227-234 (2007).

Happer, W., "Optical pumping", Rev. Mod. Phys., 44 (2), 169-249 (1972).

Purcell, E.M., Field, G.B., "Influence of collisions upon population of hyperfine states in hydrogen", Astrophys. J., 124, 542 (1956).

Ledbetter, M.P., Savukov, I.M., Acosta, V.M., Budker, D. and Romalis, M.V., "Spin-exchange-relaxation-free magnetometry with Cs vapor." Physical Review A, 77(3), 033408 (2008).

Bloom, A. L., "Principles of operation of the rubidium vapor magnetometer." Applied Optics 1(1), 61-68 (1962).

Bell, W.E., and Bloom, A.L., "Optically driven spin precession." Physical Review Letters 6, (6), 280 (1961).

Roberts, G., Holmes, N., Alexander, N., Boto, E., Leggett, J., Hill, R.M., Shah, V., Rea, M., Vaughan, R., Maguire, E.A. and Kessler, K., "Towards OPM-MEG in a virtual reality environment." NeuroImage, 199, 408-417 (2019).

Zhang, R., Xiao, W., Ding, Y., Feng, Y., Peng, X., Shen, L., Sun, C., Wu, T., Wu, Y., Yang, Y. and Zheng, Z., "Recording brain activities in unshielded Earth's field with optically pumped atomic magnetometers." Science Advances, 6(24) (2020).

De Cheveigné, A., Wong, D.D., Di Liberto, G.M., Hjortkjaer, J., Slaney, M. and Lalor, E., "Decoding the auditory brain with canonical component analysis." NeuroImage, 172, 206-216 (2018).

Mellinger, J., Schalk, G., Braun, C., Preissl, H., Rosenstiel, W., Birbaumer, N. and Kübler, A., "An MEG-based brain-computer interface (BCI)." Neuroimage, 36(3), 581-593 (2007).

Wolpaw, J.R., McFarland, D.J., Neat, G.W. and Forneris, C.A., "An EEG-based brain-computer interface for cursor control." Electroencephalography and clinical neurophysiology, 78(3), 252-259 (1991).

Lightfoot, G., "Summary of the N1-P2 cortical auditory evoked potential to estimate the auditory threshold in adults". Seminars in hearing, 37(1), 1 (2016).

Virtanen, J., Ahveninen, J., Ilmoniemi, R. J., Näätänen, R., & Pekkonen, E., "Replicability of MEG and EEG measures of the auditory N1/N1m-response." Electroencephalography and Clinical Neurophysiology/Evoked Potentials Section, 108(3), 291-298 (1998).

Gascoyne, L., Furlong, P. L., Hillebrand, A., Worthen, S. F., & Witton, C., "Localising the auditory N1m with event-related beamformers: localisation accuracy following bilateral and unilateral stimulation." Scientific reports, 6(1), 1-9 (2016).

Borna, A., Carter, T.R., Goldberg, J.D., Colombo, A.P., Jau, Y.Y., Berry, C., McKay, J., Stephen, J., Weisend, M. and Schwindt, P.D., "A 20-channel magnetoencephalography system based on optically pumped magnetometers." Physics in Medicine & Biology, 62(23), 8909 (2017).

Pyragius, T., Marin Florez, H., & Fernholz, T. (2019). A Voigt effect based 3D vector magnetometer. Physical Review A, 100(2), https://doi.org/10.1103/PhysRevA.100.023416.

Rui Zhang, Rahul Mhaskar, Ken Smith, Easswar Balasubramaniam, Mark Prouty. "All Optical Scalar Atomic Magnetometer Capable of Vector Measurement," Submitted on Nov. 17, 2020. https://arxiv.org/abs/2011.08943; Geometrics, Inc., San Jose, CA, 95131, USA.

Arjen Stolk, Ana Todorovic, Jan-Mathijs Schoffelen, and Robert Oostenveld. "Online and offline tools for head movement compensation in MEG." Neuroimage 68 (2013): 39-48.

Bagherzadeh, Yasaman, Daniel Baldauf, Dimitrios Pantazis, and Robert Desimone. "Alpha synchrony and the neurofeedback control of spatial attention." Neuron 105, No. 3 (2020): 577-587.

Allred, J. C., Lyman, R. N., Kornack, T. W., & Romalis, M. V. (2002). High-sensitivity atomic magnetometer unaffected by spin-exchange relaxation. Physical review letters, 89(13), 130801.

Balabas et al. Polarized alkali vapor with minute-long transverse spin-relaxation time, Phys. Rev. Lett. 105, 070801—Published Aug. 12, 2010.

Barbieri, F., Trauchessec, V., Caruso, L., Trejo-Rosillo, J., Telenczuk, B., Paul, E., . . . & Ouanounou, G. (2016). Local recording of biological magnetic fields using Giant Magneto Resistance-based micro-probes. Scientific reports, 6, 39330.

Dmitry Budker and Michael Romalis, "Optical Magnetometry," Nature Physics, 2008, https://arxiv.org/abs/physics/0611246v1.

Anthony P. Colombo, Tony R. Carter, Amir Borna, Yuan-Yu Jau, Cort N. Johnson, Amber L. Dagel, and Peter D. D. Schwindt, "Four-channel optically pumped atomic magnetometer for magnetoencephalography," Opt. Express 24, 15403-15416 (2016).

Dang, H.B. & Maloof, A.C. & Romalis, Michael. (2009). Ultra-high sensitivity magnetic field and magnetization measurements with an atomic magnetometer. Applied Physics Letters. 97. 10.1063/1.3491215.

Donley, E.A. & Hodby, E & Hollberg, L & Kitching, J. (2007). Demonstration of high-performance compact magnetic shields for chip-scale atomic devices. The Review of scientific instruments. 78. 083102.

Hämäläinen, Matti & Hari, Riitta & Ilmoniemi, Risto J. & Knuutila, Jukka & Lounasmaa, Olli V. Apr. 1993. Magnetoencephalograph—theory, instrumentation, and applications to noninvasive studies of the working human brain. Reviews of Modern Physics. vol. 65, Issue 2. 413-497.

Hunter, D. and Piccolomo, S. and Pritchard, J. D. and Brockie, N. L. and Dyer, T. E. and Riis, E. (2018) Free-induction-decay magnetometer based on a microfabricated Cs vapor cell. Physical Review Applied (10).ISSN 2331-7019.

Jiménez-Martínez, R., Griffith, W. C., Wang, Y. J., Knappe, S., Kitching, J., Smith, K., & Prouty, M. D. (2010). Sensitivity comparison of Mx and frequency-modulated bell-bloom Cs magnetometers in a microfabricated cell. IEEE Transactions on Instrumentation and Measurement, 59(2), 372-378.

Kiwoong Kim, Sarno Begus, Hui Xia, Seung-Kyun Lee, Vojko Jazbinsek, Zvonko Trontelj, Michael V. Romalis, Multi-channel atomic magnetometer for magnetoencephalography: A configuration study. NeuroImage 89 (2014) 143-151 http://physics.princeton.edu/romalis/papers/Kim_2014.pdf.

Knappe, Svenja & Sander, Tilmann & Trahms, Lutz. (2012). Optically-Pumped Magnetometers for MEG. Magnetoencephalography: From Signals to Dynamic Cortical Networks. 993-999. 10.1007/978-3-642-33045-2_49.

(56) References Cited

OTHER PUBLICATIONS

Kominis, I.K., Kornack, T.W., Allred, J.C. and Romalis, M.V., 2003. A subfemtotesla multichannel atomic magnetometer. Nature, 422(6932), p. 596.

Korth, H., K. Strohbehn, F. Tejada, A. G. Andreou, J. Kitching, S. Knappe, S. J. Lehtonen, S. M. London, and M. Kafel (2016), Miniature atomic scalarmagnetometer for space based on the rubidium isotope 87Rb, J. Geophys. Res. Space Physics, 121, 7870-7880, doi: 10.1002/2016JA022389.

Lenz, J. and Edelstein, S., 2006. Magnetic sensors and their applications. IEEE Sensors journal, 6(3), pp. 631-649.

Li, S & Vachaspati, Pranjal & Sheng, Dehong & Dural, Nezih & Romalis, Michael. (2011). Optical rotation in excess of 100 rad generated by Rb vapor in a multipass cell. Phys. Rev. A. 84. 10.1103/PhysRevA.84.061403.

Maze, J. R., Stanwix, P. L., Hodges, J. S., Hong, S., Taylor, J. M., Cappellaro, P., . . . & Yacoby, A. (2008). Nanoscale magnetic sensing with an individual electronic spin in diamond. Nature, 455(7213), 644.

Sander TH, Preusser J, Mhaskar R, Kitching J, Trahms L, Knappe S. Magnetoencephalography with a chip-scale atomic magnetometer. Biomed Opt Express. 2012;3(5):981-90.

J. Seltzer, S & Romalis, Michael. (2010). High-temperature alkali vapor cells with antirelaxation surface coatings. Journal of Applied Physics. 106. 114905-114905. 10.1063/1.3236649.

Seltzer, S. J., and Romalis, M.V., "Unshielded three-axis vector operation of a spin-exchange-relaxation-free atomic magnetometer." Applied physics letters 85.20 (2004): 4804-4806.

Sheng, Dong & R. Perry, Abigail & Krzyzewski, Sean & Geller, Shawn & Kitching, John & Knappe, Svenja. (2017). A microfabricated optically-pumped magnetic gradiometer. Applied Physics Letters. 110. 10.1063/1.4974349.

Sheng, Dehong & Li, S & Dural, Nezih & Romalis, Michael. (2013). Subfemtotesla Scalar Atomic Magnetometry Using Multipass Cells. Physical review letters. 110. 160802. 10.1103/PhysRevLett.110.160802.

Volkmar Schultze et al. An Optically Pumped Magnetometer Working in the Light-Shift Dispersed Mz Mode, Sensors 2017, 17, 561; doi:10.3390/s17030561.

Fang, J. and Qin, J., 2012. In situ triaxial magnetic field compensation for the spin-exchange-relaxation-free atomic magnetometer. Review of Scientific Instruments, 83(10), p. 103104.

Joon Lee, Hyun & Shim, Jeong & Moon, Han Seb & Kim, Kiwoong. (2014). Flat-response spin-exchange relaxation free atomic magnetometer under negative feedback. Optics Express. 22. 10.1364/OE.22.019887.

Griffith, Clark & Jimenez-Martinez, Ricardo & Shah, Vishal & Knappe, Svenja & Kitching, John. (2009). Miniature atomic magnetometer integrated with flux concentrators. Applied Physics Letters—Appl Phys Lett. 94. 10.1063/1.3056152.

Lee, S.-K & Romalis, Michael. (2008). Calculation of Magnetic Field Noise from High-Permeability Magnetic Shields and Conducting Objects with Simple Geometry. Journal of Applied Physics. 103. 084904-084904. 10.1063/1.2885711.

Vovrosh, Jamie & Voulazeris, Georgios & Petrov, Plamen & Zou, Ji & Gaber Beshay, Youssef & Benn, Laura & Woolger, David & Attallah, Moataz & Boyer, Vincent & Bongs, Kai & Holynski, Michael. (2018). Additive manufacturing of magnetic shielding and ultra-high vacuum flange for cold atom sensors. Scientific Reports. 8. 10.1038/s41598-018-20352-x.

Kim, Young Jin & Savukov, I. (2016). Ultra-sensitive Magnetic Microscopy with an Optically Pumped Magnetometer. Scientific Reports. 6. 24773. 10.1038/srep24773.

Navau, Carles & Prat-Camps, Jordi & Sanchez, Alvaro. (2012). Magnetic Energy Harvesting and Concentration at a Distance by Transformation Optics. Physical review letters. 109. 263903. 10.1103/PhysRevLett.109.263903.

Orang Alem, Rahul Mhaskar, Ricardo Jiménez-Martínez, Dong Sheng, John LeBlanc, Lutz Trahms, Tilmann Sander, John Kitching, and Svenja Knappe, "Magnetic field imaging with microfabricated optically-pumped magnetometers," Opt. Express 25, 7849-7858 (2017).

Slocum et al., Self-Calibrating Vector Magnetometer for Space, https://esto.nasa.gov/conferences/estc-2002/Papers/B3P4(Slocum).pdf.

Dupont-Roc, J & Haroche, S & Cohen-Tannoudji, C. (1969). Detection of very weak magnetic fields (10-9gauss) by 87Rb zero-field level crossing resonances. Physics Letters A—Phys Lett A. 28. 638-639. 10.1016/0375-9601(69) 90480-0.

J. A. Neuman, P. Wang, and A. Gallagher, Robust high-temperature sapphire cell for metal vapors, Review of Scientific Instruments, vol. 66, Issue 4, Apr. 1995, pp. 3021-3023.

Borna, Amir, et al. "A 20-channel magnetoencephalography system based on optically pumped magnetometers." Physics in Medicine & Biology 62.23 (2017): 8909.

R. E. Slocum & L. J. Ryan, Design and operation of the minature vector laser magnetometer, Nasa Earth Science Technology Conference 2003.

Schoenmaker, Jeroen & R Pirota, K & Teixeira, Julio. (2013). Magnetic flux amplification by Lenz lenses. The Review of scientific instruments. 84. 085120. 10.1063/1.4819234.

Hu, Yanhui & Hu, Zhaohui & Liu, Xuejing & Li, Yang & Zhang, Ji & Yao, Han & Ding, Ming. (2017). Reduction of far off-resonance laser frequency drifts based on the second harmonic of electro-optic modulator detection in the optically pumped magnetometer. Applied Optics. 56. 5927. 10.1364/AO.56.005927.

Masuda, Y & Ino, T & Skoy, Vadim & Jones, G.L. (2005). 3He polarization via optical pumping in a birefringent cell. Applied Physics Letters. 87. 10.1063/1.2008370.

A.B. Baranga et al., An atomic magnetometer for brain activity imaging, Real Time Conference 2005. 14th IEEE—NPSS. pp. 417-418.

Larry J. Ryan, Robert E. Slocum, and Robert B. Steves, Miniature Vector Laser Magnetometer Measurements of Earth's Field, May 10, 2004, 4 pgs.

Lorenz, V. O., Dai, X., Green, H., Asnicar, T. R., & Cundiff, S. T. (2008). High-density, high-temperature alkali vapor cell. Review of Scientific Instruments, 79(12), 4 pages.

F. Jackson Kimball, D & Dudley, J & Li, Y & Thulasi, Swecha & Pustelny, Szymon & Budker, Dmitry & Zolotorev, Max. (2016). Magnetic shielding and exotic spin-dependent interactions. Physical Review D. 94. 10.1103/PhysRevD.94.082005.

Huang, Haichao, et al. "Single-beam three-axis atomic magnetometer." Applied Physics Letters 109.6 (2016): 062404. (Year: 2016).

Scott Jeffrey Seltzer: "Developments in alkali-metal atomic magnetometry", Nov. 1, 2008 (Nov. 1, 2008), XP055616618, ISBN: 978-0-549-93355-7 Retrieved from the Internet: URL:http://physics.princeton.edu/atomic/romalis/papers/Seltzer%20Thesis.pdf [retrieved on Aug. 29, 2019] pp. 148-159.

Haifeng Dong et al: "Atomic-Signal-Based Zero-Field Finding Technique for Unshielded Atomic Vector Magnetometer", IEEE Sensors Journal, IEEE Service Center, New York, NY, US, vol. 13, No. 1, Jan. 1, 2013 (Jan. 1, 2013), pp. 186-189.

Boto, E, Holmes, N, Leggett, J, Roberts, G, Shah, V, Meyer, SS, Muñoz, LD, Mullinger, KJ, Tierney, TM, Bestmann, S, Barnes, GR, Bowtell, R & Brookes, MJ 2018, 'Moving magnetoencephalography towards real world applications with a wearable system', Nature, vol. 555, pp. 657-661.

Ijsselsteijn, R & Kielpinski, Mark & Woetzel, S & Scholtes, Theo & Kessler, Ernst & Stolz, Ronny & Schultze, V & Meyer, H-G. (2012). A full optically operated magnetometer array: An experimental study. The Review of scientific instruments. 83. 113106. 10.1063/1.4766961.

Tierney, T. M., Holmes, N., Meyer, S. S., Boto, E., Roberts, G., Leggett, J., . . . Barnes, G. R. (2018). Cognitive neuroscience using wearable magnetometer arrays: Non-invasive assessment of language function. NeuroImage, 181, 513-520.

Manon Kok, Jeroen D. Hol and Thomas B. Schon (2017), "Using Inertial Sensors for Position and Orientation Estimation", Foundations and Trends in Signal Processing: vol. 11: No. 1-2, pp. 1-153. http://dx.doi.org/10.1561/2000000094.

(56) References Cited

OTHER PUBLICATIONS

Hill RM, Boto E, Holmes N, et al. A tool for functional brain imaging with lifespan compliance [published correction appears in Nat Commun. Dec. 4, 2019;10(1):5628]. Nat Commun. 2019;10(1):4785. Published Nov. 5, 2019. doi:10.1038/s41467-019-12486-x.

Zetter, R., Iivanainen, J. & Parkkonen, L. Optical Co-registration of MRI and On-scalp MEG. Sci Rep 9, 5490 (2019). https://doi.org/10.1038/s41598-019-41763-4.

Garrido-Jurado, Sergio, Rafael Muñoz-Salinas, Francisco José Madrid-Cuevas and Manuel J. Marín-Jiménez. "Automatic generation and detection of highly reliable fiducial markers under occlusion." Pattern Recognit. 47 (2014): 2280-2292.

Hill RM, Boto E, Rea M, et al. Multi-channel whole-head OPM-MEG: Helmet design and a comparison with a conventional system [published online ahead of print, May 29, 2020]. Neuroimage. 2020;219:116995. doi: 10.1016/j.neuroimage.2020.116995.

V. Kazemi and J. Sullivan, "One millisecond face alignment with an ensemble of regression trees," 2014 IEEE Conference on Computer Vision and Pattern Recognition, Columbus, OH, 2014, pp. 1867-1874, doi: 10.1109/CVPR.2014.241.

Holmes, N., Tierney, T.M., Leggett, J. et al. Balanced, bi-planar magnetic field and field gradient coils for field compensation in wearable magnetoencephalography. Sci Rep 9, 14196 (2019).

N. Holmes, J. Leggett, E. Boto, G. Roberts, R.M. Hill, T.M. Tierney, V. Shah, G.R. Barnes, M.J. Brookes, R. Bowtell A bi-planar coil system for nulling background magnetic fields in scalp mounted magnetoencephalography Neuroimage, 181 (2018), pp. 760-774.

J. M. Leger et. al., In-flight performance of the Absolute Scalar Magnetometer vector mode on board the Swarm satellites, Earth, Planets, and Space (2015) 67:57.

Alexandrov, E. B., Balabas, M. V., Kulyasov, V. N., Ivanov, A. E., Pazgalev, A. S., Rasson, J. L., . . . (2004). Three-component variometer based on a scalar potassium sensor. Measurement Science and Technology, 15(5), 918-922.

Gravrand, O., Khokhlov, A., & JL, L. M. (2001). On the calibration of a vectorial 4He pumped magnetometer. Earth, planets and space , 53 (10), 949-958.

Borna, Amir & Carter, Tony & Colombo, Anthony & Jau, Y-Y & McKay, Jim & Weisend, Michael & Taulu, Samu & Stephen, Julia & Schwindt, Peter. (2018). Non-Invasive Functional-Brain-Imaging with a Novel Magnetoencephalography System. 9 Pages.

Vrba J, Robinson SE. Signal processing in magnetoencephalography. Methods. 2001;25(2):249-271. doi:10.1006/meth.2001.1238.

Uusitalo M and Ilmoniemi R., 1997, Signal-space projection method for separating MEG or EEG into components. Med. Biol. Comput. (35) 135-140.

Taulu S and Kajola M., 2005, Presentation of electromagnetic multichannel data: the signal space separation method. J. Appl. Phys. (97) 124905 (2005).

Taulu S, Simola J and Kajola M., 2005, Applications of the signal space separation method. IEEE Trans. Signal Process. (53) 3359-3372 (2005).

Taulu S, Simola J., 2006, Spatiotemporal signal space separation method for rejecting nearby interference in MEG measurements. Phys. Med. Biol. (51) 1759-1768 (2006).

Johnson, et al., Magnetoencephalography with a two-color pump-probe, fiber-coupled atomic magnetometer, Applied Physics Letters 97, 243703 2010.

Zhang, et al., Magnetoencephalography using a compact multichannel atomic magnetometer with pump-probe configuration, AIP Advances 8, 125028 (2018).

Xia, H. & Ben-Amar Baranga, Andrei & Hoffman, D. & Romalis, Michael. (2006). Magnetoencephalography with an atomic magnetometer. Applied Physics Letters—Appl Phys Lett. 89. 10.1063/1.2392722.

Ilmoniemi, R. (2009). The triangle phantom in magnetoencephalography. In 24th Annual Meeting of Japan Biomagnetism and Bioelecctromagnetics Society, Kanazawa, Japan, May 28.29, 2009 (pp. 6263).

Oyama D. Dry phantom for magnetoencephalography—Configuration, calibration, and contribution. J Neurosci Methods. 2015;251:24-36. doi: 0.1016/j.jneumeth.2015.05.004.

Chutani, R., Maurice, V., Passilly, N. et al. Laser light routing in an elongated micromachined vapor cell with diffraction gratings for atomic clock applications. Sci Rep 5, 14001 (2015). https://doi.org/10.1038/srep14001.

Eklund, E. Jesper, Andrei M. Shkel, Svenja Knappe, Elizabeth A. Donley and John Kitching. "Glass-blown spherical microcells for chip-scale atomic devices." (2008).

Jiménez-Martínez R, Kennedy DJ, Rosenbluh M, et al. Optical hyperpolarization and NMR detection of 129Xe on a microfluidic chip. Nat Commun. 2014;5:3908. Published May 20, 2014. doi:10.1038/ncomms4908.

Boto, Elena, Sofie S. Meyer, Vishal Shah, Orang Alem, Svenja Knappe, Peter Kruger, T. Mark Fromhold, et al. "A New Generation of Magnetoencephalography: Room Temperature Measurements Using Optically-Pumped Magnetometers." NeuroImage 149 (Apr. 1, 2017): 404-14.

Bruno, A. C., and P. Costa Ribeiro. "Spatial Fourier Calibration Method for Multichannel SQUID Magnetometers." Review of Scientific Instruments 62, No. 4 (Apr. 1, 1991): 1005-9.

Chella, Federico, Filippo Zappasodi, Laura Marzetti, Stefania Della Penna, and Vittorio Pizzella. "Calibration of a Multichannel MEG System Based on the Signal Space Separation Method." Physics in Medicine and Biology 57 (Jul. 13, 2012): 4855-70.

Pasquarelli, A, M De Melis, Laura Marzetti, Hans-Peter Müller, and S N Erné. "Calibration of a Vector-MEG Helmet System." Neurology & Clinical Neurophysiology□: NCN 2004 (Feb. 1, 2004): 94.

Pfeiffer, Christoph, Lau M. Andersen, Daniel Lundqvist, Matti Hämäläinen, Justin F. Schneiderman, and Robert Oostenveld. "Localizing On-Scalp MEG Sensors Using an Array of Magnetic Dipole Coils." PLoS One 13, No. 5 (May 10, 2018): e0191111.

Vivaldi, Valentina, Sara Sommariva, and Alberto Sorrentino. "A Simplex Method for the Calibration of a MEG Device." Communications in Applied and Industrial Mathematics 10 (Jan. 1, 2019): 35-46.

Nagel, S., & Spüler, M. (2019). Asynchronous non-invasive high-speed BCI speller with robust non-control state detection. Scientific Reports, 9(1), 8269.

Thielen, J., van den Broek, P., Farquhar, J., & Desain, P. (2015). Broad-Band Visually Evoked Potentials: Re(con)volution in Brain-Computer Interfacing. PLoS One, 10(7), e0133797. https://doi.org/10.1371/journal.pone.0133797.

J. Kitching, "Chip-scale atomic devices," Appl. Phys. Rev. 5(3), 031302 (2018), 39 pages.

\* cited by examiner

SYSTEMS AND METHODS WITH ANGLED INPUT BEAMS FOR AN OPTICALLY PUMPED MAGNETOMETER

CROSS-REFERENCE TO RELATED APPLICATIONS

This application claims the benefit of U.S. Provisional Patent Application Ser. Nos. 62/865,049, filed Jun. 21, 2019, and 62/913,000, filed Oct. 9, 2019, both of which are incorporated herein by reference in their entireties.

FIELD

The present disclosure is directed to the area of magnetic field measurement systems using an array of optically pumped magnetometers (OPMs). The present disclosure is also directed to magnetic field measurement systems and methods with a prism optic to produce angled input beams for an optically pumped magnetometer.

BACKGROUND

In the nervous system, neurons propagate signals via action potentials. These are brief electric currents which flow down the length of a neuron causing chemical transmitters to be released at a synapse. The time-varying electrical currents within an ensemble of neurons generate a magnetic field. Magnetoencephalography (MEG), the measurement of magnetic fields generated by the brain, is one method for observing these neural signals.

Existing systems for observing or measuring MEG typically utilize superconducting quantum interference devices (SQUIDs) or collections of discrete optically pumped magnetometers (OPMs). SQUIDs require cryogenic cooling which is bulky and expensive and requires a lot of maintenance which preclude their use in mobile or wearable devices. Many conventional applications of optically pumped magnetometers to MEG involve a single vapor cell inside a 1 to 2 cm package, preventing or hindering spatial resolution beyond this range. Thermal management and magnetic cross talk also pose other practical limitations to achieving high spatial resolution with discrete magnetometers.

BRIEF SUMMARY

One embodiment is an optically pumped magnetometer device that includes a first vapor cell having a light input window; a first light source configured to produce a first light beam; a first prism optic configured to receive the first light beam from the first light source and redirect the first light beam into the first vapor cell at a non-normal direction relative to the light input window of the first vapor cell; and a first light detector configured to receive the first light beam after passing through the first vapor cell.

In at least some embodiments, the optically pumped magnetometer device further includes a first collimating lens disposed in a path of the first light beam between the first vapor cell and the first prism optic. In at least some embodiments, the optically pumped magnetometer device further includes a first monitor detector, where the first prism optic and the first vapor cell are configured to redirect a portion of the first light beam to the first monitor detector prior to passage of a remainder the first light beam through the first vapor cell. In at least some embodiments, the optically pumped magnetometer device further includes a board, where the first light source and the first monitor detector are mounted on the board.

In at least some embodiments, the first prism optic is disposed adjacent the light input window of the first vapor cell. In at least some embodiments, the first prism optic forms the light input window of the first vapor cell. In at least some embodiments, the first vapor cell is physically disposed between the first light detector and the first prism optic. In at least some embodiments, the optically pumped magnetometer device further includes a first polarization control optic disposed to receive the first light beam. In at least some embodiments, the first prism is formed of molded plastic or glass.

In at least some embodiments, the optically pumped magnetometer device further includes a second light source configured to produce a second light beam, where the first prism optic configured to receive the second light beam from the second light source and redirect the second light beam into a different portion of the first vapor cell than the first light beam at a non-normal direction relative to the light input window of the first vapor cell; and a second light detector configured to receive the second light beam after passing through the first vapor cell.

In at least some embodiments, the optically pumped magnetometer device further includes a second vapor cell including a light input window; a second light source configured to produce a second light beam, where the first prism optic configured to receive the second light beam from the second light source and redirect the second light beam into the second vapor cell at a non-normal direction relative to the light input window of the second vapor cell; and a second light detector configured to receive the second light beam after passing through the second vapor cell.

In at least some embodiments, the optically pumped magnetometer device further includes a second light source configured to produce a second light beam; a second prism optic configured to receive the second light beam from the second light source and redirect the second light beam into a different portion of the first vapor cell than the first light beam at a non-normal direction relative to the light input window of the first vapor cell; and a second light detector configured to receive the second light beam after passing through the first vapor cell.

In at least some embodiments, the optically pumped magnetometer device further includes a second vapor cell including a light input window; a second light source configured to produce a second light beam; a second prism optic configured to receive the second light beam from the second light source and redirect the second light beam into the second vapor cell at a non-normal direction relative to the light input window of the second vapor cell; and a second light detector configured to receive the second light beam after passing through the second vapor cell.

In at least some embodiments, the first and second prism optics are coupled together as a single optical element. In at least some embodiments, the first prism optic includes a first sloped face and a second sloped face, where the first sloped face is configured to receive the first light beam and the second sloped face is configured to receive the second light beam.

In at least some embodiments, the optically pumped magnetometer device further includes a first monitor detector and a second monitor detector, where the first prism optic and the first vapor cell are configured to redirect a portion of the first light beam to the first monitor detector prior to passage of a remainder the first light beam through the first vapor cell and to redirect a portion of the second light beam to the second monitor detector prior to passage of a remainder the second light beam through the second vapor cell.

In at least some embodiments, the optically pumped magnetometer device further includes a first board, where the first light source, second light source, first monitor detector, and second monitor detector are mounted on the first board. In at least some embodiments, the optically pumped magnetometer device further includes a second board, where the first light detector and second light detector are mounted on the second board.

Another embodiment is a magnetic field measurement system that includes any of the optically pumped magnetometer devices described above and at least one magnetic field generator disposed around the optically pumped magnetometer device. In at least some embodiments, the magnetic field measurement system further includes a computing device configured to receive signals from the optically pumped magnetometer device.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present disclosure is directed to the area of magnetic field measurement systems using an array of optically pumped magnetometers (OPMs). The present disclosure is also directed to magnetic field measurement systems and methods with a prism optic to produce angled input beams for an optically pumped magnetometer.

Although the present disclosure utilizes magnetoencephalography (MEG) to exemplify the arrays, systems, and methods described herein, it will be understood that the arrays, systems, and methods can be used in any other suitable application.

Herein the terms "ambient background magnetic field" and "background magnetic field" are interchangeable and used to identify the magnetic field or fields associated with sources other than the magnetic field measurement system and the biological source(s) (for example, neural signals from a user's brain) or other source(s) of interest. The terms can include, for example, the Earth's magnetic field, as well as magnetic fields from magnets, electromagnets, electrical devices, and other signal or field generators in the environment, except for the magnetic field generator(s) that are part of the magnetic field measurement system.

The terms "gas cell", "vapor cell", and "vapor gas cell" are used interchangeably herein. Below, a vapor cell containing alkali metal vapor is described, but it will be recognized that other vapor cells can contain different gases or vapors for operation.

An optically pumped magnetometer (OPM) is a basic component used in optical magnetometry to measure magnetic fields. While there are many types of OPMs, in general magnetometers operate in two modalities: vector mode and scalar mode. In vector mode, the OPM can measure one, two, or all three vector components of the magnetic field; while in scalar mode the OPM can measure the total magnitude of the magnetic field.

Vector mode magnetometers measure a specific component of the magnetic field, such as the radial and tangential components of magnetic fields with respect to the scalp of the human head. Vector mode OPMs often operate at zero-field and may utilize a spin exchange relaxation free (SERF) mode to reach femto-Tesla sensitivities. A SERF mode OPM is one example of a vector mode OPM, but other vector mode OPMs can be used at higher magnetic fields. These SERF mode magnetometers can have high sensitivity but may not function in the presence of magnetic fields higher than the linewidth of the magnetic resonance of the atoms of about 10 nT, which is much smaller than the magnetic field strength generated by the Earth. As a result, conventional SERF mode magnetometers often operate inside magnetically shielded rooms that isolate the sensor from ambient magnetic fields including Earth's magnetic field.

Magnetometers operating in the scalar mode can measure the total magnitude of the magnetic field. (Magnetometers in the vector mode can also be used for magnitude measurements.) Scalar mode OPMs often have lower sensitivity than SERF mode OPMs and are capable of operating in higher magnetic field environments.

The magnetic field measurement systems described herein can be used to measure or observe electromagnetic signals generated by one or more sources (for example, neural signals or other biological sources). The system can measure biologically generated magnetic fields and, at least in some embodiments, can measure biologically generated magnetic fields in an unshielded or partially shielded environment. Aspects of a magnetic field measurement system will be exemplified below using magnetic signals from the brain of a user; however, biological signals from other areas of the body, as well as non-biological signals, can be measured using the system. In at least some embodiments, the system can be a wearable MEG system that can be used outside a magnetically shielded room.

Figure 1A:
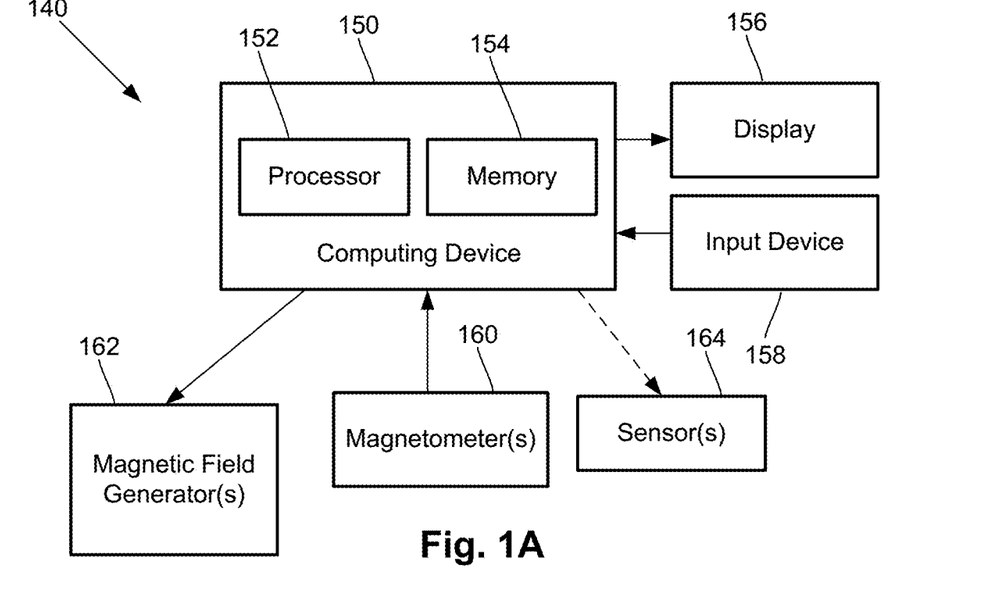
FIG. 1A is a schematic block diagram of one embodiment of a magnetic field measurement system, according to the invention.

FIG. 1A is a block diagram of components of one embodiment of a magnetic field measurement system 140. The system 140 can include a computing device 150 or any other similar device that includes a processor 152 and a memory 154, a display 156, an input device 158, one or more magnetometers 160 (for example, an array of magnetometers) which can be OPMs, one or more magnetic field generators 162, and, optionally, one or more sensors 164. The system 140 and its use and operation will be described herein with respect to the measurement of neural signals arising from signal sources in the brain of a user as an example. It will be understood, however, that the system can be adapted and used to measure other neural signals, other biological signals, as well as non-biological signals.

The computing device 150 can be a computer, tablet, mobile device, field programmable gate array (FPGA), microcontroller, or any other suitable device for processing information or instructions. The computing device 150 can be local to the user or can include components that are non-local to the user including one or both of the processor 152 or memory 154 (or portions thereof). For example, in at least some embodiments, the user may operate a terminal that is connected to a non-local computing device. In other embodiments, the memory 154 can be non-local to the user.

The computing device 150 can utilize any suitable processor 152 including one or more hardware processors that may be local to the user or non-local to the user or other components of the computing device. The processor 152 is configured to execute instructions, as described below.

Any suitable memory 154 can be used for the computing device 150. The memory 154 illustrates a type of computer-readable media, namely computer-readable storage media. Computer-readable storage media may include, but is not limited to, volatile, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 156 can be any suitable display device, such as a monitor, screen, or the like, and can include a printer. In some embodiments, the display is optional. In some embodiments, the display 156 may be integrated into a single unit with the computing device 150, such as a tablet, smart phone, or smart watch. In at least some embodiments, the display is not local to the user. The input device 158 can be, for example, a keyboard, mouse, touch screen, track ball, joystick, voice recognition system, or any combination thereof, or the like. In at least some embodiments, the input device is not local to the user.

The magnetic field generator(s) 162 can be, for example, Helmholtz coils, solenoid coils, planar coils, saddle coils, electromagnets, permanent magnets, or any other suitable arrangement for generating a magnetic field. As an example, the magnetic field generator 162 can include three orthogonal sets of coils to generate magnetic fields along three orthogonal axes. Other coil arrangements can also be used. The optional sensor(s) 164 can include, but are not limited to, one or more magnetic field sensors, position sensors, orientation sensors, accelerometers, image recorders, or the like or any combination thereof.

The one or more magnetometers 160 can be any suitable magnetometer including, but not limited to, any suitable optically pumped magnetometer. Arrays of magnetometers are described in more detail herein. In at least some embodiments, at least one of the one or more magnetometers (or all of the magnetometers) of the system is arranged for operation in the SERF mode. Examples of magnetic field measurement systems or methods of making such systems or components for such systems are described in U.S. Patent Application Publications Nos. 2020/0072916; 2020/0056263; 2020/0025844; 2020/0057116; 2019/0391213; 2020/0088811; 2020/005,711; 2020/0109481; and 2020/0123416; U.S. patent application Ser. Nos. 16/573,394; 16/573,524; 16/679,048; 16/741,593; 16/752,393; 16/850,380 and 16/850,444, and U.S. Provisional Patent Application Ser. Nos. 62/689,696; 62/699,596; 62/719,471; 62/719,475; 62/719,928; 62/723,933; 62/732,327; 62/732,791; 62/741,777; 62/743,343; 62/747,924; 62/745,144; 62/752,067; 62/776,895; 62/781,418; 62/796,958; 62/798,209; 62/798,330; 62/804,539; 62/826,045; 62/827,390; 62/836,421; 62/837,574; 62/837,587; 62/842,818; 62/855,820; 62/858,636; 62/860,001; 62/865,049; 62/873,694; 62/874,887; 62/883,399; 62/883,406; 62/888,858; 62/895,197; 62/896,929; 62/898,461; 62/910,248; 62/913,000; 62/926,032; 62/926,043; 62/933,085; 62/960,548; 62/971,132; and 62/983,406, all of which are incorporated herein by reference in their entireties. The magnetometers, arrangements, prism optics, and the like described below can be incorporated in the magnetic field measurements systems and methods described in these cited references.

Figure 1B:
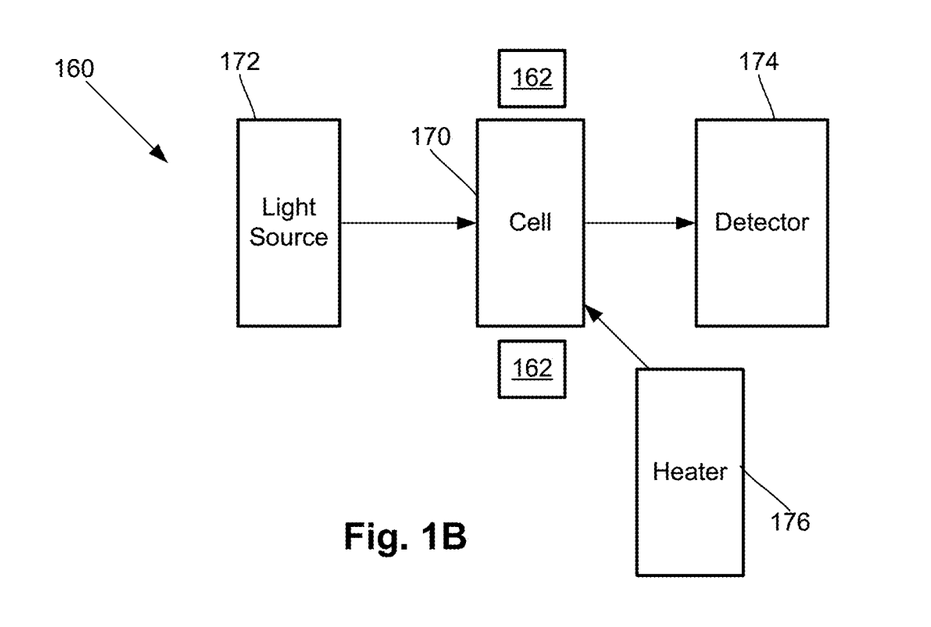
FIG. 1B is a schematic block diagram of one embodiment of a magnetometer, according to the invention.

FIG. 1B is a schematic block diagram of one embodiment of a magnetometer 160 which includes an alkali metal vapor cell 170 (also referred to as a "cell" or "gas cell"); a heating device 176 to heat the cell 170; a light source 172; and a detector 174. In addition, coils of a magnetic field generator 162 can be positioned around the vapor cell 170. The vapor cell 170 can include, for example, an alkali metal vapor (for example, rubidium in natural abundance, isotopically enriched rubidium, potassium, or cesium, or any other suitable alkali metal such as lithium, sodium, or francium) and, optionally, one, or both, of a quenching gas (for example, nitrogen) or a buffer gas (for example, nitrogen, helium, neon, or argon). In some embodiments, the vapor cell may include the alkali metal atoms in a prevaporized form prior to heating to generate the vapor.

The light source 172 can include, for example, a laser to, respectively, optically pump the alkali metal atoms and to probe the vapor cell. The light source 172 may also include optics (such as lenses, waveplates, collimators, polarizers, and objects with reflective surfaces) for beam shaping and polarization control and for directing the light from the light source to the cell and detector. Examples of suitable light sources include, but are not limited to, a diode laser (such as a vertical-cavity surface-emitting laser (VCSEL), distributed Bragg reflector laser (DBR), or distributed feedback laser (DFB)), light-emitting diode (LED), lamp, or any other suitable light source. In some embodiments, the light source 172 may include two light sources: a pump light source and a probe light source.

The detector 174 can include, for example, an optical detector to measure the optical properties of the transmitted light field amplitude, phase, or polarization, as quantified through optical absorption and dispersion curves, spectrum, or polarization or the like or any combination thereof. Examples of suitable detectors include, but are not limited to, a photodiode (PD), charge coupled device (CCD) array, CMOS array, camera, photodiode array, single photon avalanche diode (SPAD) array, avalanche photodiode (APD) array, or any other suitable optical sensor array that can measure the change in transmitted light at the optical wavelengths of interest.

Figure 2:
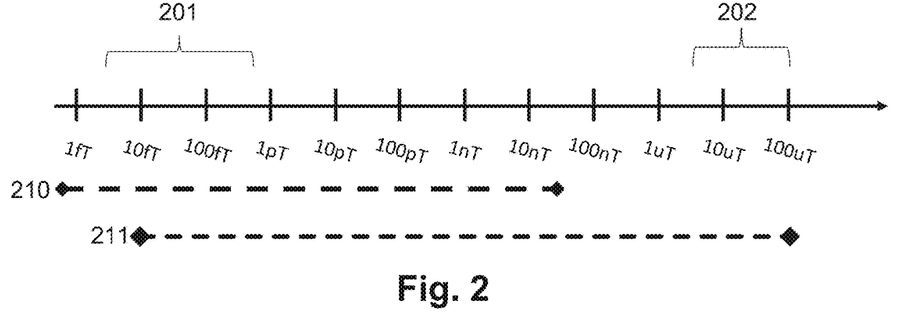
FIG. 2 shows a magnetic spectrum with lines indicating dynamic ranges of magnetometers operating in different modes.

FIG. 2 shows the magnetic spectrum from 1 fT to 100 µT in magnetic field strength on a logarithmic scale. The magnitude of magnetic fields generated by the human brain are indicated by range 201 and the magnitude of the background ambient magnetic field, including the Earth's magnetic field, by range 202. The strength of the Earth's magnetic field covers a range as it depends on the position on the Earth as well as the materials of the surrounding environment where the magnetic field is measured. Range 210 indicates the approximate measurement range of a magnetometer (e.g., an OPM) operating in the SERF mode (e.g., a SERF magnetometer) and range 211 indicates the approximate measurement range of a magnetometer operating in a scalar mode (e.g., a scalar magnetometer.) Typically, a SERF magnetometer is more sensitive than a scalar magnetometer but many conventional SERF magnetometers typically only operate up to about 0 to 200 nT while the scalar magnetometer starts in the 10 to 100 fT range but extends above 10 to 100 µT.

In the nervous system, neurons communicate with one another via action potentials. These are brief electric currents which flow down the length of a neuron causing chemical transmitters to be released at a synapse. The time-varying electrical current within the neuron generates a magnetic field, which propagates through the human head and can be measured using either a Superconducting Quantum Interference Device (SQUID) or an Optically Pumped Magnetometer (OPM). It is desirable to detect magnetic field components in all three spatial axes. However, doing this with single-beam transmission-mode OPM sensors can involve some tradeoffs because such OPMs naturally provide the best sensitivity only to fields that are orthogonal to the optical pumping beam. Two perpendicular beams can therefore be employed, where each provides response along two response axes, with one axis shared between the four total response vectors. However, this approach is most easily adapted to alkali vapor cells with transparent sides, such as those formed by blown-glass cells, which facilitate transverse-beam access. On the other hand, for manufacturability, it may desirable to use wafer-scale anodically-bonded vapor cells, which only have optical access through windows on two opposite sides. Therefore, it may be desirable to configure beams that can pump the vapor along two perpendicular directions, where at least one of those directions is not normal to the input window face.

One conventional solution is to provide the optical pumping beam(s) directed through the window at 45-degrees with respect to the window normal vector, such that the beam-transverse sensitive axes are not simply degenerate with respect to the window plane. With such techniques, either a single such angled beam can be coupled with external modulation fields that generate all three axes of vector information, or two such beams can be displaced from each other in the vapor cell and directed perpendicular to each other, generating a complete basis vector space with simple external modulation.

In each case, however, these conventional angled-beam implementations use laser sources and collimation optics that occupy substantial additional space around the vapor cell—in many cases using substantial portions of an optical table to generate the angled beam routes. Such an approach may be difficult to scale to high channel count for magnetoencephalography (MEG) or other applications, where relatively small sensor-to-sensor spacing is desired.

In addition, the use of discrete optics with independent degrees of freedom (for example, turning mirrors) can produce difficult alignment problems for a large array, as well as relatively high cost.

Spherical micromachined cells have been developed, but these cells require more delicate handling during fabrication and packaging than traditional flat-window MEMS cells. In addition, antireflection coatings can be more difficult to integrate into such cells.

Alternatively, mirrors in the vapor space have been used to redirect the beams after transmission through the input window. However, as the beam approaches the mirror, within roughly one beam diameter, the atoms are pumped by the superposition of the input and reflected beams, which may not satisfy the desired vector space coverage requirement. For large cells, and especially with a pump/probe arrangement, this may be a useful approach, because the beams can be made small with respect to the two propagation zones (before and after the internal mirror), and the pump can be detuned so that attenuation effects can be controlled. In a compact cell where the beam diameter is of the same magnitude as the total cell volume, and especially with a single-beam approach, such an approach is likely not very effective.

Another conventional approach uses an input diffraction grating, coupled with internal mirrors formed by the natural silicon facets after a wet-etch process, to redirect a beam transverse to the input window. In addition to suffering from the beam-overlap issue mentioned above for a single pump beam, this approach can also suffer from low optical efficiency, which means that the sensitivity and dynamic range of the OPM may not be optimized with the full optical power of the laser source.

In contrast to these conventional approaches, as described herein, a magnetic field measurement system (or other OPM system) can employ one or more prism optics to facilitate light beam routing. In at least some embodiments, the prism optic can be compact or can be molded or both compact and molded. In at least some embodiments, the prism optic(s) can facilitate angled input beam routing for complete vector reconstruction of magnetic fields in an alkali metal vapor cell. In at least some embodiments, the prism optic(s) can produce a total footprint of each sensitive region in the vapor cell that is relatively small.

Figure 3A:
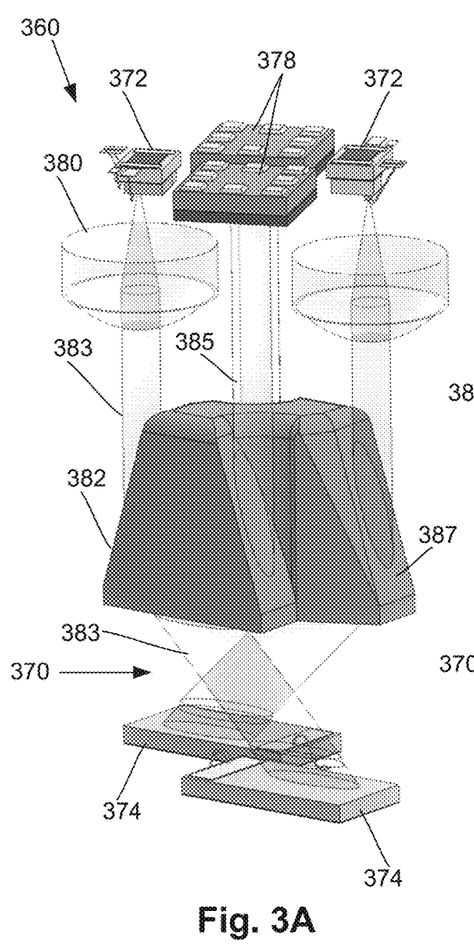
FIG. 3A is a schematic perspective view of one embodiment of portions of two optically pumped magnetometers including a prism optic, but with the vapor cell(s) hidden, according to the invention.
Figure 3B:
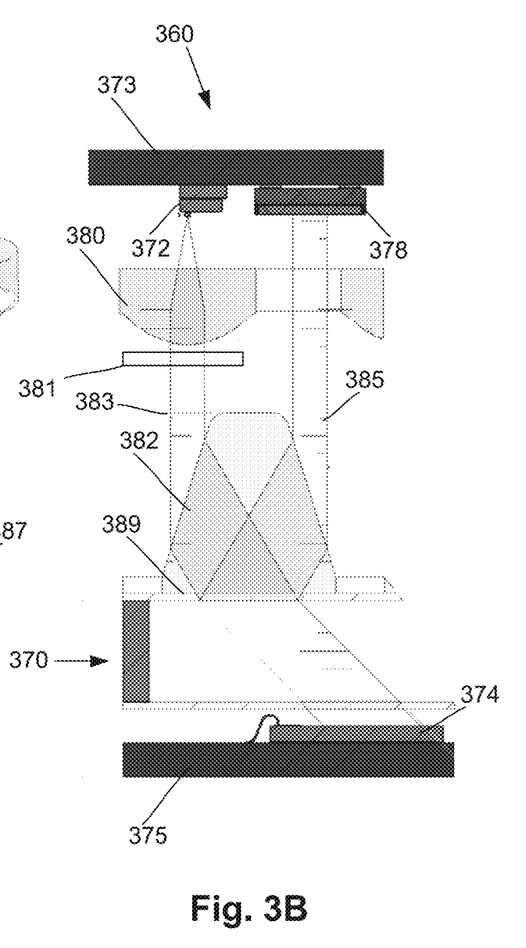
FIG. 3B is a schematic cross-sectional view of one embodiment of a portion of an optically pumped magnetometer including a prism optic, according to the invention.

FIG. 3A illustrates one embodiment of selected components of a magnetic field measurement system (or other OPM system) and a magnetometer 360 including two light sources 372, two light detectors 374, two monitor detectors (e.g., photodiodes) 378, two prism optics 382, and two collimating lenses 380. The vapor cell is hidden in this Figure, but the position of the vapor cell is indicated by the arrow 370. FIG. 3B illustrates another embodiment of selected components of a magnetic field measurement system (or other OPM system) and a magnetometer 360 utilizing only one of each component. FIG. 3B also illustrates a polarization control optic 381 that can be embodied, for example, by a thin flat quarter-wave plate, placed in the collimated beam space following the collimated lens 380. The polarization control optic 381 can be positioned in other locations along the optical path including, but not limited to, between the prism optic 382 and the vapor cell 370. The polarization control optic 381 is omitted from FIGS. 3A, 3C, 3D and FIGS. 4 to 6 for clarity of illustration.

FIGS. 3A and 3B illustrate: an input prism optic 382 that follows a collimating lens 380. The prism optic 382 redirects the light beam 383 at a steep angle towards the vapor cell 370. In at least some embodiments, to support an array of light beams 383 and due to the convoluted geometry, the prism optic 382 is formed using molding techniques. In at least some embodiments, such as the illustrated embodiment of FIG. 3A, the unit cell of the prism optic can have four total optical faces 387 to allow for two input light beams 383 in this zone (each with a monitor output face, as described below). In at least some embodiments, to support an array of sensitive regions, the prism optic unit cell can be tiled (or replicated along one or more dimensions to interact with more than two light beams 383) and a single monolithic part (see, for example, FIG. 4) can be molded for an arrangement with more than two light sources 372.

FIG. 3B is a cross-sectional view of one optically-pumped region, showing a portion of the vapor cell 370 (3.0 mm thick in this embodiment), collimation lens 380, routing prism optic 382, as well as carrier boards 373, 375 for the light source 372/monitor detector 378 and light detector 374, respectively. In this embodiment, the prism optic 382 is adjacent or disposed on the vapor cell 370. In other embodiments, the prism optic 382 may be spaced apart from the vapor cell 370. In other embodiments, the prism optic 382 and window 389 of the vapor cell 370 can be made of a single molded optic in a sealing glass (such as borosilicate). The combination prism optic 382/window 389 can be attached, for instance via anodic bonding to other walls of the vapor cell 370. Such an arrangement could eliminate one optical interface between separate prism optic/vapor cell window components.

Dimensions in the following description are provided for one embodiment and used for illustration purposes. It will be understood that other embodiments may utilize different dimensions. After collimation, a 1.0 mm diameter incident light beam 383 is refracted by the routing prism optic 382, which in this embodiment employs an angle-of-incidence of 72.73 degrees, to give a final light beam angle of 45 degrees with respect to the normal of the window 389 of the vapor cell 370 once in the vapor cell 370. For use in a magnetoencephalography (MEG) system, the user's head would likely be located towards the bottom of FIG. 3B (below the transmitted-beam light detector 374), so that the vapor cell standoff from neural sources in the brain of the user can be relatively small or minimized. This embodiment shows refraction for a routing prism optic 382 of optical index 1.4 (similar to moldable optical silicone) and vapor cell glass windows 389 of index 1.5.

It will be recognized that the light beam 383 can enter the vapor cell 370 at angles other than 45 degrees with respect to the normal of the input window 389. Although a 45 degree angle allows for implementation of orthonormal response axes, the magnetometer would also function with multi-axis responsivity—and even full 3D coverage—as long as two more light beams 383 have a nonzero cross product, such that their response vectors span 3D space.

Figure 3C:
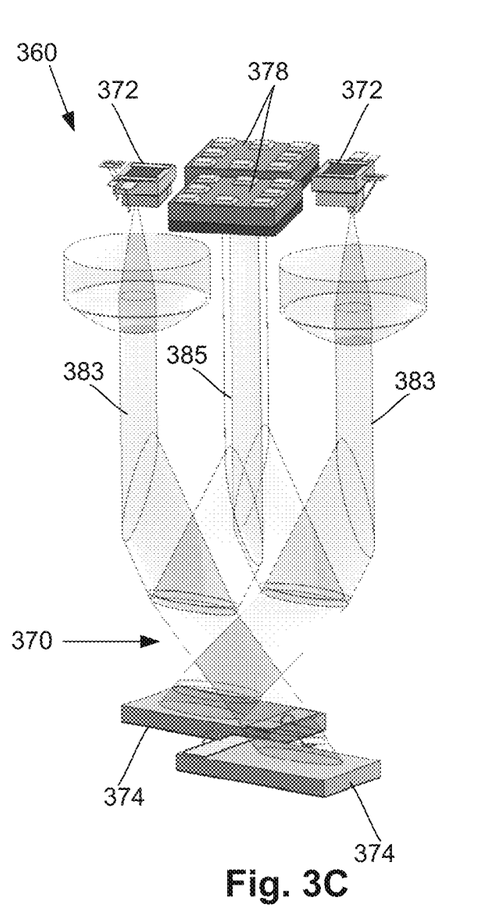
FIG. 3C is a schematic perspective view of the two optically pumped magnetometers of FIG. 3A, but with the prism optic and vapor cell(s) hidden in order to show the light beam paths, according to the invention.

In FIGS. 3A and 3C, the vapor cell 370 can be a single vapor cell in which the light beams from the two light sources 372 are directed to two different (in at least some embodiments, non-overlapping) portions of the single vapor cell. In other embodiments, the vapor cell 370 can represent two distinct vapor cells with the light beams from the two light sources 472 directed to different vapor cells.

Figure 3D:
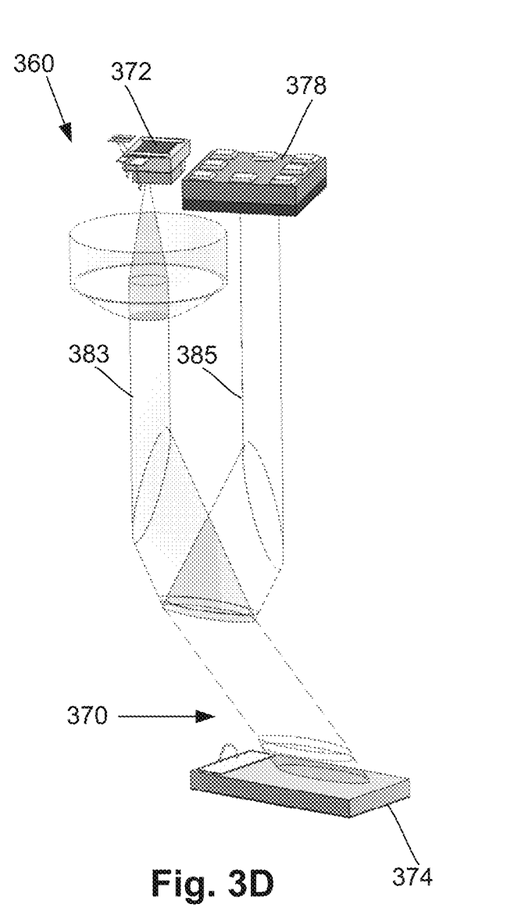
FIG. 3D is a schematic perspective view of the optically pumped magnetometer of FIG. 3B, but with the prism optic and vapor cell hidden in order to show the light beam paths, according to the invention.

FIGS. 3C and 3D illustrate the embodiments of FIGS. 3A and 3B, respectively, with the prism optics and vapor cells removed to illustrate the routing of the light beam(s) 383, 385. FIGS. 3C and 3D illustrate collimation and routing of a light beam 383 from a light source 372 into a vapor cell (not shown but position is indicated by arrow 370) at an angle with respect to the normal of the input window 389 (FIG. 3B) with eventual transmitted-beam detection by the light detector 374. The light detectors 374 can be assumed to span the X, Y plane, with Z taken normal to the vapor cell window 389 (FIG. 3B). In the two beam arrangement of FIGS. 3A and 3C, the second copy of the arrangement is rotated 180 degrees around the Z axis and slightly displaced to prevent double-pumping any region of the vapor in the vapor cell 370. The two light beams 383 are perpendicular to each other, which provides for their responsive axes together to span 3D vector space.

In at least some embodiments, a monitor beam 385 is picked off and detected by a monitor detector 378 (e.g. photodiode) which optionally may be co-located on the same board or substrate as the light source. In at least some embodiments, the monitor beam 385 can be formed by reflection of a small fraction of the light from the vapor cell inner glass surface which interfaces with the vapor. A monitor beam 385 can be particularly useful at high incident optical power where excess intensity noise generates spurious signal that could be corrected by suitable power monitoring. It will be recognized that the monitor detectors 378 and the faces on the prism optic 382 to support the direction of light to the light monitor detectors are optional. An alternative embodiment could eliminate the monitor beam 385 and also may employ antireflection coatings to increase light intensity in the vapor cell 370.

Figure 4:
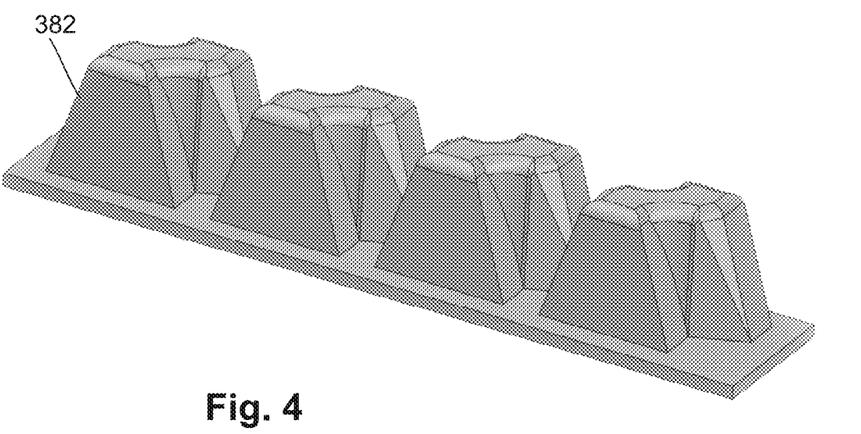
FIG. 4 is a schematic perspective view of an array of prism optics formed a single optical element, according to the invention.

FIG. 4 illustrates one embodiment of a 4×1 array of dual-input-beam prism optics 382 joined as a single optical element. In at least some embodiments, such prism optics 382 and optical elements are formable by a molding process using, for example, moldable glass or optical silicone or any other suitable material. Other glasses or polymers can be used for as the molded material for the prism optic 382. Each specific material, when employed as a refractive prism, will redirect the light beam at an angle that is specific to the material's optical index. Therefore, the specific facet angles of the prism optic 382 can be tuned to match the materials used.

Figure 5:
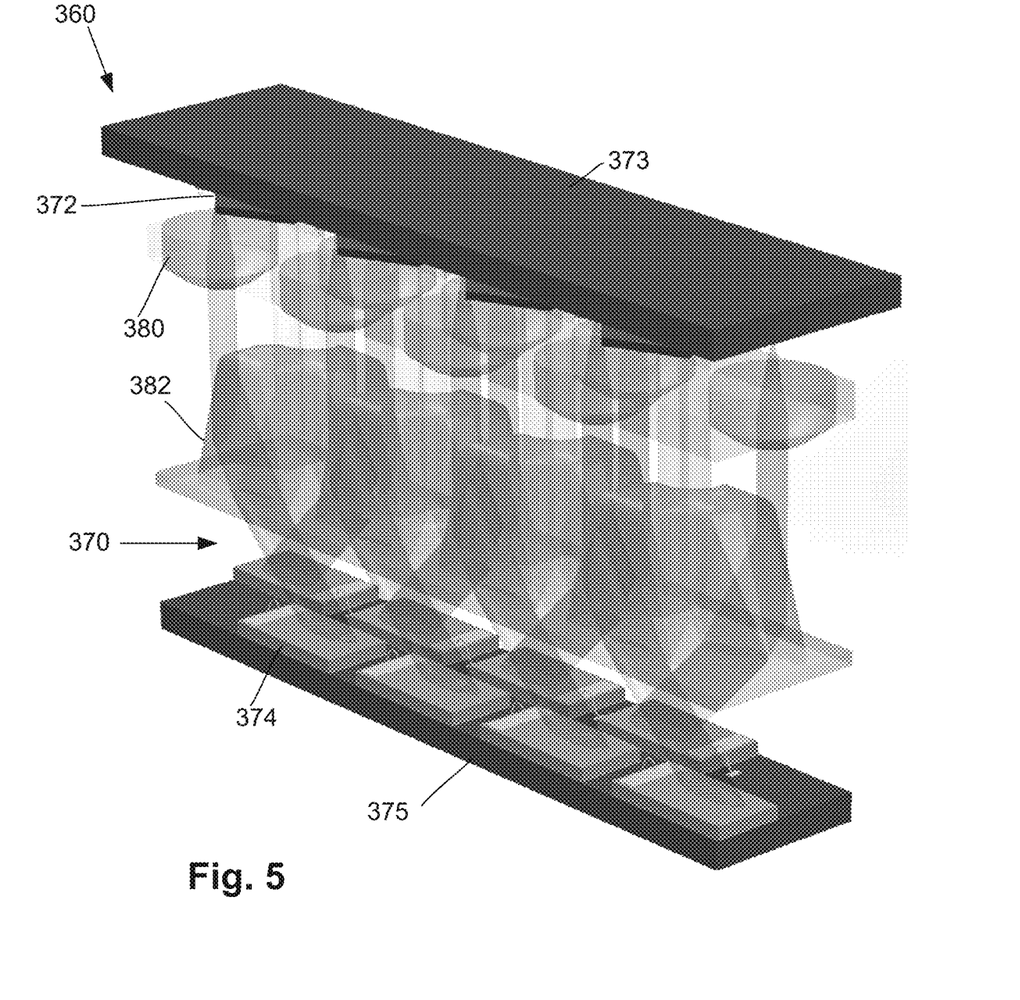
FIG. 5 is a schematic perspective view of an array of eight optically pumped magnetometers utilizing the array of prism optics of FIG. 4, according to the invention.

FIG. 5 illustrates one embodiment of a 4×2 linear array of optically-pumped magnetometers 360 all utilizing single shared vapor cell 370 (which is not shown for clarity). Each sensor includes a light source 372, collimating lens 380, prism optic 382, and detector 374.

Figure 6:
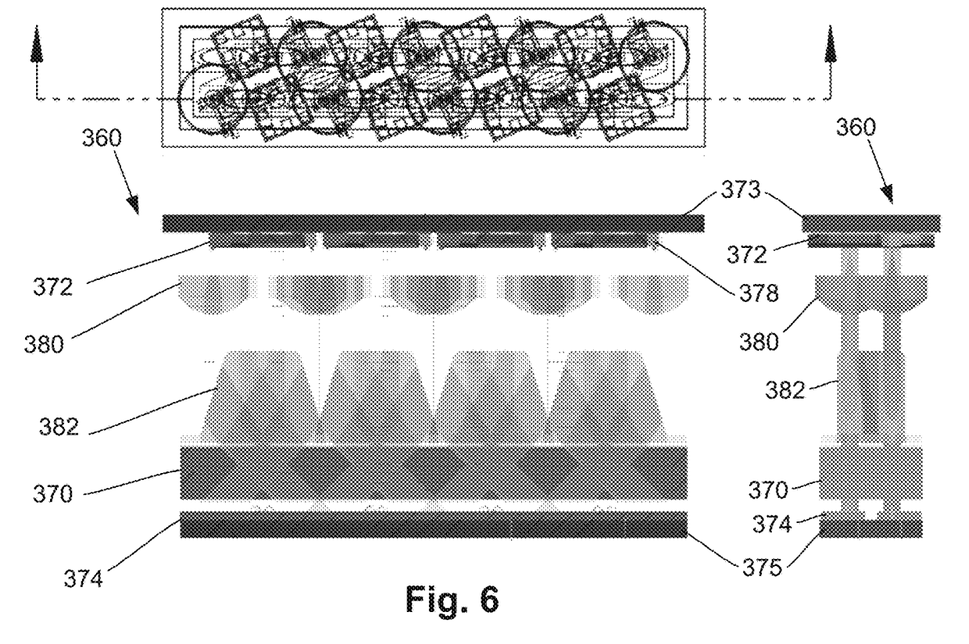
FIG. 6 presents schematic top and two side views of the array of optically pumped magnetometers of FIG. 5, according to the invention.

FIG. 6 illustrates top and two side views of the 4×2 array of FIG. 5. The optically-pumped regions in this embodiment are tiled in the XY plane (where Z is normal to the windows) by, for example, a 2.4 mm pitch in the direction transverse to the prism optic's incident plane and by, for example, a 6.5 mm pitch in the other direction.

The vapor cell 370 can be a single vapor cell in which the light beams from the different light sources 372 are directed to different (in at least some embodiments, non-overlapping) portions of the single vapor cell. In other embodiments, the vapor cell 370 can represent multiple distinct vapor cells with the light beams from the light sources 372 directed to different vapor cells. In yet other embodiments, the vapor cell 370 can represent multiple distinct vapor cells with one or more light beams from the light sources 372 being directed to individual ones of the vapor cells.

In at least some embodiments, a prism optic 382 allows a compact interface between one or more light sources 372 and one or more vapor cells 370 with corresponding one or more optically pumped regions, where each region is pumped by its single input beam at a substantial angle with respect to the input window normal. In at least some embodiments, the prism optic 382 can be integrated at one of several stages in an assembly process, including at the full wafer scale where it can be diced along with the rest of the vapor cell stack. In at least some embodiments, the prism optic 382 is arranged with respect to the vapor cell window either by direct attachment via transparent adhesive layer, such as spin-on epoxy, or by optomechanical support.

A pair of perpendicular beams naturally provides four sensitive vector outputs, two of which are nominally degenerate (the degenerate response vector lies along the axis perpendicular to the plane formed by the two pump beam vectors), as long as the pumped regions are close to each other so that field gradients between them are negligible. In at least some embodiments, the degenerate vector can be used for technical noise reduction and as a monitor of the sensor responsivity, since any discrepancy between the two readings on that axis serves as an observation of non-ideal device performance.

Because at least some embodiments of a single-beam transmission mode atomic magnetometer make use of a substantially circularly-polarized optical pumping beam in the vapor cell, suitable phase-controlled coatings may be beneficial at most or all optical interfaces in the device. In at least some embodiments, these coatings may also implement anti-reflection capabilities and controlled-reflection capabilities as may be desirable at the interface that picks off the monitor beam.

In at least some embodiments, the architecture of the device surrounding the vapor cell 370 and prism optic 382 allows for a compact array of OPM sensor regions, with relatively small or minimal standoff to the magnetic field source, for example, for a MEG system, neural currents in the brain of a user.

In at least some embodiments with multiple light sources 372, the light sources are all arranged on a shared plane which, in some embodiments, can be a PCB (printed circuit board) 373, as illustrated in FIGS. 3B, 5, and 6. Such arrangements can provide an array of magnetometers 360 (e.g., sensors) with an suitable array size or pitch. In at least some embodiments, a minimum pitch can be set by, for example, component/beam overlap dimensions. In at least some embodiments, a power-monitor light beam 385 of each input light beam 383 is picked off before it enters the vapor cell 370 and directed to a monitor detector 378 which, in at least some embodiments, can be conveniently co-located on the same circuit board 373 as the light source 372. The light detectors 374 may also be coplanar and can be tiled along with the other components to support an array of magnetometers 360.

In at least some embodiments, the magnetometer 360 (or an array of magnetometers) have one or more of the following features: a relatively small standoff distance between the vapor cell 370 and the magnetic field source, such as the brain of the user; a relatively high channel count; or the use of materials and processes that are mass-manufacturable at the wafer scale.

At least some current methods of commercially-available OPM MEG technology rely on transmission-mode optical detection of the pump beam, which for an angled input beam generates an angled output beam. If the vapor cell windows are substantially tangential to the user's scalp in a MEG system—as is also compatible with high-density channel packing—then the standoff distance from the field source to the alkali metal vapor depends on compact detection of the transmitted light. In contrast, in at least some embodiments, the light detectors 374 are positioned relatively close—and parallel to—the output window of the vapor cell 370 which can be desirable to reduce or minimize the volume of components between the user's head and the vapor cell. This compact approach means that the light detector 374 is operated at a temperature substantially close to the elevated vapor cell temperature, although noise from the light detector 374 preferably remains sufficiently low to facilitate highly sensitive operation.

In other embodiments, the light detector 374 can be positioned apart from the vapor cell 370 so that the light detector is not substantially heated by the vapor cell. For example, the light beam 383 could be reflected after passing through the vapor cell and directed toward the light detector 374, as disclosed in magnetometer arrangements presented in the patent application references cited above. As an example, the light detectors 374 can be attached, or disposed near, the light source board 373 and the light beam 383 can be reflected beam through a return path through the vapor cell 370 to the light detector. Such a light beam route may be more complicated and with higher alignment precision and would likely include a mirror as part of the magnetometer which would take up excess volume in the space between the user's head and the vapor cell, all of which may increase the standoff distance.

In at least some embodiments, the prism optic 382 could also include some or all of the beam collimation functions that are performed by a separate collimating lens 380 or lens array in the embodiments illustrated in FIGS. 3A to 6. Such a prism optic/collimator can be achieved by, for example, providing appropriate curvature of the incident faces of the prism optic. In at least some embodiments, providing cylindrical curvature on one or more faces of the prism optic may partially or completely counteract the beam-stretching effect of the prism optic so that the optical beam inside the vapor cell could be more radially symmetric about the propagation vector than the spatially-elliptical beam in at least some of the embodiments presented above. In at least some embodiments, such cylindrical optical curvature can be implemented at the collimating lens 380 or at the prism optic 382 or at yet another separate optic.

In at least some embodiments, any optical coatings on any of the components of the magnetometer can be selected to provide specific polarization states, some of which may include substantial elliptical or linear polarization for the light beam 383.

In at least some embodiments, the prism optic 382 can be functionalized, by, for example, choice of primary material, material additive, or integrated component, to assist with thermal management of the vapor cell 370. The vapor cell 370 is heated for operation, and may use anisotropic heating to preferentially condense alkali metal atoms away from the optical input regions. In at least some embodiments, the prism optic 382 can serve as a heater, heat spreader, or thermal insulator depending on construction or material.

In at least some embodiments, a magnetometer with just one light beam—as long as it enjoys a substantial angle with respect to the normal of the vapor cell window 389—will give response to magnetic field components normal to the vapor cell window. While that embodiment might not span 3D space, it may nonetheless be desirable for some applications, such as recording scalp-normal emanating magnetic fields in MEG. This is to be contrasted with a transmission-mode device where the light beam(s) are directed purely normal to the local scalp surface, which gives only response to scalp-tangent fields.

In at least some embodiments, a multi-light source approach (such as an arrangement with separate pump and probe light sources) can be implemented with a refractive prism optic 382 as disclosed herein, which may use a second probe beam either substantially co-propagating with the pump light beam, or alternatively directed transverse to it, as can be achieved by a tiling of light sources with strong overlap of two adjacent light beams. In at least some of these embodiments, the probe light beam can be a low-intensity, far-detuned light source that interacts with the separately pumped atoms.

At least some embodiments include a molded prism optic 382 that can be mass-manufactured, integrated at the wafer scale, and used to direct optical beams with high power efficiency into a vapor cell 370 at high incident angle with respect to the window 389 of the vapor cell. At least some embodiments can provide a magnetometer 360 with responsivity to source magnetic field components directed substantially normal to the vapor cell window 389, as well as substantially transverse to the windows, with a footprint substantially similar to the light beam diameter. At least some embodiments can provide a magnetometer that also naturally provides for a power monitor beam 385. At least some embodiments can provide a magnetometer that naturally allows for relatively small standoff distance from the magnetic field source. At least some embodiments can include suitable pairing of beams disposed substantially perpendicular to each other to provide a magnetometer system with 3-axis responsivity to incident magnetic fields, where each sensitive region is a single transmission-mode magnetometer.

In at least some embodiments, the beam routing prism optic 382 facilitates dense packing of an array of sensitive regions in one or more vapor cells 370. In at least some embodiments, the light beam angles allow for optoelectronic components with minimal or lower precision alignment compared to optical designs where beams substantially retrace their input propagation paths and, therefore, must be detected very close to the light source. In at least some embodiments, a compact packing architecture provide by use of the prism optic 382 allows planar tiling of the light sources 372, light detectors 374, and collimation and polarization-control optics into matching arrays of magnetometers or sensors. In at least some embodiments, the light beams 383 are naturally disposed in this architecture so as to never cross themselves or each other in the vapor cell 370, allowing efficient optical pumping along preferred directions. In at least some embodiments, degenerate pairing of sensitive response vectors naturally provides a technical noise monitor mechanism.

The above specification provides a description of the invention and its manufacture and use. Since many embodiments of the invention can be made without departing from the spirit and scope of the invention, the invention also resides in the claims hereinafter appended.

What is claimed as new and desired to be protected by Letters Patent of the United States is:

1. An optically pumped magnetometer device, comprising:
    a first vapor cell comprising a light input window;
    a first light source configured to produce a first light beam;
    a first refractive prism optic configured to receive the first light beam from the first light source and refractively redirect the first light beam into the first vapor cell at a non-normal direction relative to the light input window of the first vapor cell; and
    a first light detector configured to receive the first light beam after passing through the first vapor cell.

2. The optically pumped magnetometer device of claim 1, further comprising a first collimating lens disposed in a path of the first light beam between the first light source and the first refractive prism optic.

3. The optically pumped magnetometer device of claim 1, further comprising a first monitor detector, wherein the first refractive prism optic and the first vapor cell are configured to redirect a portion of the first light beam to the first monitor detector prior to passage of a remainder the first light beam through the first vapor cell.

4. The optically pumped magnetometer device of claim 3, further comprising a board, wherein the first light source and the first monitor detector are mounted on the board.

5. The optically pumped magnetometer device of claim 1, wherein the first refractive prism optic is disposed adjacent the light input window of the first vapor cell.

6. The optically pumped magnetometer device of claim 1, wherein the first refractive prism optic forms the light input window of the first vapor cell.

7. The optically pumped magnetometer device of claim 1, wherein the first vapor cell is physically disposed between the first light detector and the first refractive prism optic.

8. The optically pumped magnetometer device of claim 1, further comprising a first polarization control optic disposed to receive the first light beam.

9. The optically pumped magnetometer device of claim 1, further comprising
    a second light source configured to produce a second light beam, wherein the first refractive prism optic is configured to receive the second light beam from the second light source and redirect the second light beam into a different portion of the first vapor cell than the first light beam at a non-normal direction relative to the light input window of the first vapor cell; and
    a second light detector configured to receive the second light beam after passing through the first vapor cell.

10. The optically pumped magnetometer device of claim 9, wherein the first refractive prism optic comprises a first sloped face and a second sloped face, wherein the first sloped face is configured to receive the first light beam and the second sloped face is configured to receive the second light beam.

11. The optically pumped magnetometer device of claim 9, further comprising a first monitor detector and a second monitor detector, wherein the first refractive prism optic and the first vapor cell are configured to redirect a portion of the first light beam to the first monitor detector prior to passage of a remainder the first light beam through the first vapor cell and to redirect a portion of the second light beam to the second monitor detector prior to passage of a remainder the second light beam through the second vapor cell.

12. The optically pumped magnetometer device of claim 11, further comprising a first board, wherein the first light source, second light source, first monitor detector, and second monitor detector are mounted on the first board.

13. The optically pumped magnetometer device of claim 12, further comprising a second board, wherein the first light detector and second light detector are mounted on the second board.

14. The optically pumped magnetometer device of claim 1, further comprising
   a second vapor cell comprising a light input window;
   a second light source configured to produce a second light beam, wherein the first refractive prism optic configured to receive the second light beam from the second light source and redirect the second light beam into the second vapor cell at a non-normal direction relative to the light input window of the second vapor cell; and
   a second light detector configured to receive the second light beam after passing through the second vapor cell.

15. The optically pumped magnetometer device of claim 1, further comprising
   a second light source configured to produce a second light beam;
   a second refractive prism optic configured to receive the second light beam from the second light source and redirect the second light beam into a different portion of the first vapor cell than the first light beam at a non-normal direction relative to the light input window of the first vapor cell; and
   a second light detector configured to receive the second light beam after passing through the first vapor cell.

16. The optically pumped magnetometer device of claim 15, wherein the first and second refractive prism optics are coupled together as a single optical element.

17. The optically pumped magnetometer device of claim 1, further comprising
   a second vapor cell comprising a light input window;
   a second light source configured to produce a second light beam;
   a second refractive prism optic configured to receive the second light beam from the second light source and redirect the second light beam into the second vapor cell at a non-normal direction relative to the light input window of the second vapor cell; and
   a second light detector configured to receive the second light beam after passing through the second vapor cell.

18. The optically pumped magnetometer device of claim 1, wherein the first refractive prism optic is formed of molded plastic or glass.

19. A magnetic field measurement system, comprising
   the optically pumped magnetometer device of claim 1; and
   at least one magnetic field generator disposed around the optically pumped magnetometer device.

20. The magnetic field measurement system of claim 19, further comprising a computing device configured to receive signals from the optically pumped magnetometer device.

* * * * *